United States Patent

Linker et al.

[11] Patent Number: 5,739,349
[45] Date of Patent: Apr. 14, 1998

[54] PROCESS AND INTERMEDIATES FOR THE PREPARATION OF TRIAZOLINONES

[75] Inventors: Karl-Heinz Linker, Leverkusen; Wilhelm Haas, Pulheim; Kurt Findeisen, Leverkusen; Hans-Joachim Diehr, Wuppertal, all of Germany

[73] Assignee: Bayer Aktiengesellschaft, Leverkusen, Germany

[21] Appl. No.: 784,653

[22] Filed: Jan. 21, 1997

Related U.S. Application Data

[62] Division of Ser. No. 528,375, Sep. 14, 1995, Pat. No. 5,639,891, which is a division of Ser. No. 336,943, Nov. 10, 1994, Pat. No. 5,475,115.

[30] Foreign Application Priority Data

Nov. 18, 1993 [DE] Germany ............... 43 39 412.4

[51] Int. Cl.[6] ................................ C07D 249/12
[52] U.S. Cl. .................. 548/264.6; 548/263.2; 548/263.6; 548/263.8
[58] Field of Search .............. 548/263.2, 263.6, 548/263.8, 264.6

[56] References Cited

U.S. PATENT DOCUMENTS

| | | | |
|---|---|---|---|
| 3,780,052 | 12/1973 | Cebalo et al. | |
| 4,120,864 | 10/1978 | Seidel et al. | 548/264.2 |
| 5,405,861 | 4/1995 | Itoh et al. | 548/268.6 |

FOREIGN PATENT DOCUMENTS

| | | |
|---|---|---|
| 139183 | 2/1985 | European Pat. Off. |
| 27679 | 3/1988 | European Pat. Off. |

OTHER PUBLICATIONS

Robert–Pressard, et al., "2 –Arylindane–1,3–diones, etc." CA 112 : 7425 g, 1990.

Kroger et al., "1,2,4–triazoles. II, etc" CA 55 : 23508b,d (1961).

Duffin et al., "Structure and reactivity of, etc" CA 54 : 7696 b,c. (1960).

Aouial et al., "Fragmentation, etc.," *Organic Mass Spectr* 12 (10) pp. 638–643, 1977.

Primary Examiner—Patricia L. Morris
Attorney, Agent, or Firm—Sprung Kramer Schaefer & Briscoe

[57] ABSTRACT

The invention relates to a new process and new intermediates for the preparation of triazolinones of the general formula (I)

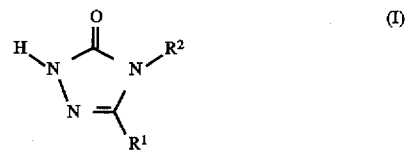

in which
$R^1$ represents in each case optionally substituted alkyl or cycloalkyl and
$R^2$ represents amino or in each case optionally substituted alkyl, alkenyl, alkinyl, alkoxy, alkylamino, dialkylamino, cycloalkyl, cycloalkylalkyl or phenyl, and to new intermediates for the preparation of triazolinones, many of which are known and which can be used as intermediates for the preparation of herbicides and insecticides.

6 Claims, No Drawings

PROCESS AND INTERMEDIATES FOR THE PREPARATION OF TRIAZOLINONES

This is a division of application Ser. No. 08/528,375, filed on Sep. 14, 1995 (now U.S. Pat. No. 5,639,891), which is a division of application Ser. No. 08/336,943, filed on Nov. 10, 1994 (now U.S. Pat. No. 5,475,115).

The invention relates to a new process and to new intermediates for the preparation of triazolinones, many of which are known and which can be used as intermediates for the preparation of herbicides and insecticides.

It is known that certain substituted triazolinones such as, for example, the compound 4-methyl-5-trifluoromethyl-2,4-dihydro-3H-1,2,4-triazole-3-one, is obtained when suitable triazolinethiones, such as, for example, the compound 4-methyl-5-trifluoromethyl-2,4-dihydro-3H-1,2,4-triazole-3-thione, are first reacted with an alkylating agent, such as, for example, methyl iodide, in the presence of an acid-binding agent, such as, for example, sodium methylate, and the resulting alkylthiotriazole derivative is isolated in the customary manner, then heated with hydrogen peroxide in the presence of acetic acid, and the product is cooled, then neutralized and worked up in the customary manner (cf. U.S. Pat. No. 3,780,052—Example 2).

It is furthermore known that the abovementioned compound 4-methyl-5-trifluoromethyl-2,4-dihydro-3H-1,2,4-triazole-3-one can also be obtained by heating 1-trifluoroacetyl-4-methylsemicarbazide at 160° C. to 180° C. and subsequent extraction with ethyl acetate and column chromatography (cf. U.S. Pat. No. 3,780,052—Example 3). However, yield and quality of the products obtained are highly unsatisfactory in both synthetic processes described.

The present application relates to a process for the preparation of triazolinones of the general formula (I)

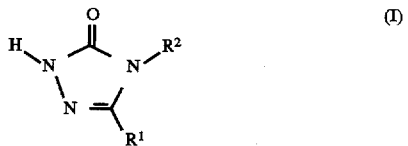

in which

R$^1$ represents in each case optionally substituted alkyl or cycloalkyl and

R$^2$ represents amino or in each case optionally substituted alkyl, alkenyl, alkinyl, alkoxy, alkylamino, dialkylamino, cycloalkyl, cycloalkylalkyl or phenyl, characterized in that alkylsulphonyltriazole derivatives of the general formula (II)

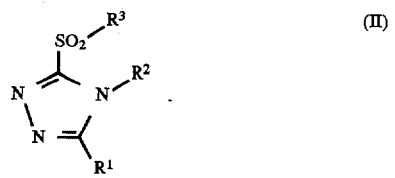

in which

R$^1$ and R$^2$ have the abovementioned meanings and

R$^3$ represents alkyl are reacted with aqueous alkali metal hydroxide solution at temperatures between 0° C. and 100° C. under atmospheric pressure and the product is acidified and then worked up in the customary manner.

Surprisingly, the process according to the invention allows the triazolinones of the general formula (I) to be obtained in a simple manner in very high yields—which are considerably improved compared with the prior art—and in high purity.

The process according to the invention is therefore a valuable enrichment of the prior art.

Compounds of the formula (I) which are preferably prepared by the process according to the invention are those in which R$^1$ represents alkyl having 1 to 6 carbon atoms which is optionally substituted by halogen, cyano or C$_1$—C$_4$-alkoxy, or represents a cycloalkyl having 3 to 6 carbon atoms which is optionally substituted by halogen, cyano or C$_1$-C$_4$-alkyl and R$^2$ represents amino, or represents alkyl, alkenyl, alkinyl, alkoxy, alkylamino or dialkylamino, each of which has up to 6 carbon atoms in the alkyl, alkenyl or alkinyl groups and each of which is optionally substituted by halogen, cyano or C$_1$-C$_4$-alkoxy, or represents C$_3$-C$_6$-cycloalkyl, C$_3$-C$_6$-cycloalkyl-C$_1$-C$_2$-alkyl or phenyl, each of which is optionally substituted by halogen, cyano, C$_1$-C$_4$-alkyl, C$_1$-C$_4$-alkoxy or C$_1$-C$_4$-alkoxy-carbonyl.

The hydrocarbon radicals mentioned in the definitions of the radicals., such as alkyl, also in combination with hetero atoms, such as in alkoxy, alkylthio or alkylamino, are straight-chain or branched, even when this is not expressly stated.

Halogen generally represents fluorine, chlorine, bromine or iodine, preferably fluorine, chlorine or bromine, in particular fluorine or chlorine.

In particular, compounds of the formula (I) which are prepared by the process according to the invention are those in which R$^1$ represents methyl, ethyl, n- or i-propyl or n-, i- or s-butyl, each of which is optionally substituted by fluorine, chlorine, bromine, cyano, methoxy or ethoxy, or represents cyclopropyl, cyclopropylmethyl, cyclobutyl, cyclopentyl or cyclohexyl, each of which is optionally substituted by fluorine, chlorine, bromine, cyano or methyl, and R$^2$ represents amino, or represents methyl, ethyl, n- or i-propyl, n-, i - or s -butyl, allyl, propargyl, methoxy, ethoxy, n- or i -propoxy, n- , i- or s-butoxy, methylamino, ethylamino, n- or i-propylamino, n -, i - or s -butylamino, dimethylamino or diethylamino, each of which is optionally substituted by fluorine, chlorine, cyano, methoxy or ethoxy, or represents cyclopropyl, cyclobutyl, cyclopentyl, cyclohexyl or phenyl, each of which is optionally substituted by fluorine, chlorine, bromine, cyano, methyl, ethyl, n- or i-propyl, methoxy-carbonyl or ethoxy-carbonyl.

A very particularly preferred group of compounds which can be prepared by the process according to the invention are the compounds of the formula (I) in which R$^1$ represents methyl, ethyl, n- or i-propyl, cyclopropyl or cyclopropylmethyl, each of which is mono-, di-, tri-, tetra-, penta-, hexa- or heptasubstituted, as appropriate, with fluorine and/or chlorine, and R$^2$ represents methyl, ethyl, n- or i-propyl, methoxy, ethoxy, methylamino, ethylamino, dimethylamino, cyclopropyl, phenyl or tolyl.

The abovementioned general definitions of radicals, or definitions of radicals whose preferred ranges have been indicated, apply to the end products of the formula (I) and, analogously, to the starting materials or intermediates required in each case for the preparation.

These definitions of radicals can be combined with each other, as desired, that is to say combinations between the abovementioned ranges of preferred compounds are also possible.

If, for example, 3-difluoromethyl-4-methyl-5-methyl-sulphonyl-4H-1,2,4-triazole and potassium hydroxide are used as starting substances, the course of the reaction in the process according to the invention can be outlined by the following equation:

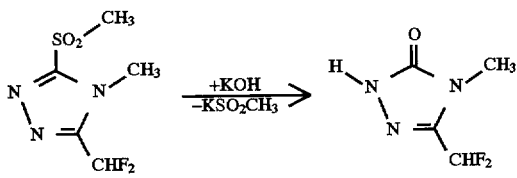

Formula (II) provides the general definition of the alkyl-sulphonyitriazole derivatives to be used as starting substances in the process according to the invention for the preparation of the compounds of the general formula (I).

In formula (II), $R^1$ and $R^2$ preferably, or in particular, have those meanings which have already been mentioned above in connection with the description of the compounds of the formula (I) as being preferred, or particularly preferred, for $R^1$ and $R^2$; $R^3$ preferably represents alkyl having 1 to 4 carbon atoms, in particular methyl or ethyl.

The starting substances of the general formula (II) are hitherto unknown from the literature; as new substances, they are a subject of the present application.

The new alkylsulphonyltriazole derivatives of the general formula (II), are obtained when alkylthiotriazole derivatives of the general formula (III)

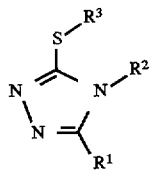 (III)

in which $R^1$, $R^2$ and $R^3$ have the abovementioned meanings, are reacted with oxidants at temperatures between 0° C. and 100° C., if appropriate in the presence of reaction auxiliaries and, if appropriate, in the presence of diluents (cf. the preparation examples).

Examples of oxidants which are suitable for this purpose are oxygen, ozone, hydrogen peroxide, chlorine, sodium hypochlorite solution, potassium permanganate, performic acid, peracetic acid, perpropionic acid and optionally halogenated perbenzoic acids.

Reaction auxiliaries which are suitable for this purpose—in particular when hydrogen peroxide is used—are mainly salts of metals of sub-groups IV, V and VI of the Periodic Table of the Elements. Examples which may be mentioned are sodium (meta)vanadate, sodium molybdate and sodium tungstate.

Diluents which are suitable for this purpose are, in particular, aliphatic, alicyclic or aromatic, optionally halogenated hydrocarbons, such as, for example, benzinc, benzene, toluene, xylene, chlorobenzene, dichlorobenzene, petroleum ether, hexane, cyclohexane, dichloromethane, chloroform, tetrachloromethane; ethers, such as diethyl ether, diisopropyl ether, dioxane, tetrahydrofuran or ethylene glycol dimethyl ether or ethyleneglycol diethyl ether; ketones, such as acetones, butsnone or methyl isobutyl ketone; nitriles, such as acetonitrile, propionitrile or benzonitrile; amides, such as N,N-dimethylformamide, N,N-dimethylacetamide, N-methyl-formanilide, N-methylpyrrolidone or hexamethylphosphoric triamide; carboxylic acids, such as formic acid, acetic acid or propionic acid, esters, such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, their mixtures with water, or pure water.

The alkylthiotriazole derivatives of the general formula (III) which are required as precursors are hitherto unknown from the literature with the exception of the compound 4-methyl-3-trifluoromethyl-5-methylthio-1H-1,2,4-triazole (cf. U.S. Pat. No. 3,780,052—Example 2); as new substances, they are a subject of the present application.

The alkylthtotriazole derivatives of the general formula (III) are obtained when triazolinethiones of the general formula (IV)

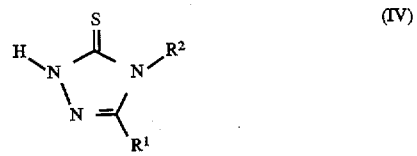 (IV)

in which $R^1$ and $R^2$ have the abovementioned meanings, are reacted with alkylating agents, such as, for example, methyl bromide, methyl iodide, ethyl bromide or ethyl iodide, at temperatures between 0° C. and 100° C., if appropriate in the presence of an acid acceptor, such as, for example, sodium hydroxide or potassium hydroxide, and, if appropriate, in the presence of a diluent, such as, for example, methanol or ethanol (cf. the preparation examples).

The triazolinethiones of the general formula (IV) are known and/or can be prepared by processes known per se (cf. U.S. Pat. No. 3,719,686 and U.S. Pat. No. 3,780,052).

The triazolinethiones of the general formula (IV) are obtained when carboxylic acids of the general formula (V)

$$R^1—CO—X \quad (V)$$

in which $R^1$ has the abovementioned meaning and

X represents hydroxyl or halogen, are reacted with alkylthiosemicarbazides of the general formula (VI)

$$R^2—NH—CS—NH—NH_2 \quad (VI)$$

in which $R^2$ has the abovementioned meaning, at temperatures between 0° C. and 100° C., (cf. the preparation examples).

The process according to the invention for the preparation of triazolinones of the general formula (I) is carried out using aqueous alkali metal hydroxide solutions. Preferably suitable for this purpose are aqueous solutions of sodium hydroxide or of potassium hydroxide.

When carrying out the process according to the invention, the reaction temperatures can be varied within a substantial range. In general, the process is carried out at temperatures between 0° C. and 100° C., preferably at temperatures between 10° C. and 80° C., in particular at temperatures between 20° C. and 60° C.

In general, the process according to the invention is carried out under atmospheric pressure. However, the process can also be carried out under elevated or reduced pressure—in general between 0.1 bar and 10 bar.

To carry out the process according to the invention for the preparation of the compounds of the formula (I), 1 to 15 mol, preferably 2 to 8 mol, of an alkali metal hydroxide dissolved in water ("aqueous alkali metal hydroxide solution") are generally employed per mol of the alkylsulphonyltriazole derivative of the formula (II).

In a preferred embodiment of the process according to the invention, the alkali metal hydroxide solution is introduced first and the alkylsulphonyltriazole of the formula (II) is metered in slowly—if appropriate with cooling. The reaction mixture is then stirred until the reaction has ended—if appropriate at elevated temperature. The mixture is subsequently acidified using an acid, preferably a protonic acid such as, for example, hydrochloric acid or sulphuric acid. If appropriate, the reaction mixture can be concentrated or diluted with water before or after the acidification step.

The reaction product can be worked up and isolated in the customary manner. For example, it is shaken with an organic solvent which is virtually immiscible with water, such as, for example, methylene chloride or ethyl acetate, and the organic phase is separated off and dried, for example using sodium sulphate. The mixture is then filtered, and the solvent is removed carefully from the filtrate by distillation under reduced pressure. The crude product which remains as residue can be employed directly for further reactions or purified further in the customary manner, for example by column chromatography and/or recrystallization.

The triazolinones of the formula (I) to be prepared by the process according to the invention can be used as intermediates for the preparation of active compounds which can be utilized agriculturally (cf. U.S. Pat. No. 3,780,052, U.S. Pat. No. 3,780,053, U.S. Pat. No. 3,780,054 and EP-A 341489).

PREPARATION EXAMPLES

Example 1

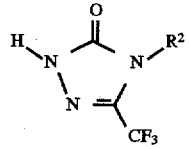

112 g (0.49 mol) of 4-methyl-3-methylsulfonyl-5-trifluoromethyl-4H-1,2,4-triazole are added to a solution of 111 g (2.78 mol) of sodium hydroxide in 1.64 liters of water and the reaction mixture is stirred for 16 hours at 50° C. The clear yellowish solution formed in this process is subsequently acidified using concentrated hydrochloric acid, then concentrated under a water pump vacuum to approximately half its volume and finally shaken with methylene chloride. After the organic phase has been separated off, the aqueous phase is re-extracted two more times using methylene chloride. The combined organic phases are dried using sodium sulphate and filtered. The solvent is then carefully removed from the filtrate by distillation under a water pump vacuum.

71 g (87% of theory) of 4-methyl-5-trifluoromethyl-2,4-dihydro-3H-1,2,4-triazole-3-one is obtained as a white powder of melting point 64° C.

Example 2

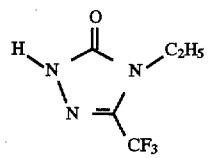

317 g (1.30 mol) of 4-ethyl-3-trifluoromethyl-5-methylsulphonyl-4H-1,2,4-triazole are added dropwise to a solution of 294 g (7.35 mol) of sodium hydroxide in 1.8 liters of water at not more than 30° C. (cooling with ice-water) and the mixture is stirred for 8 hours at 20° C. The mixture is subsequently stirred into 1.5 liters of ice-water, the pH is brought to 2–3 using concentrated hydrochloric acid, the mixture is extracted repeatedly using ethyl acetate and dried over sodium sulphate, and the solvent is evaporated.

215 g (91% of theory) of 4-ethyl-5-trifluoromethyl-2,4-dihydro-3H-1,2,4-triazole-3-one of melting point 54° C. is obtained.

Other examples of the compounds of the formula (I) which can be prepared analogously are those listed in Table 1 below.

TABLE 1

Examples of the compounds of the formula (I) which can be prepared according to the invention

| Example No. | $R^1$ | $R^2$ | physical data |
|---|---|---|---|
| 3 | $CF_3$ | $CH(CH_3)_2$ | m.p.: 46° C. |
| 4 | $CHF_2$ | $C_2H_5$ | m.p.: 41° C. |
| 5 | $CF_2Cl$ | $CH_3$ | |
| 6 | $CHF_2$ | $CH_3$ | m.p.: 116° C. |
| 7 | $CF_2CHFCl$ | $CH_3$ | m.p.: 82° C. |
| 8 | $CHF_2$ | ▷ | |
| 9 | $CF_3$ | phenyl | m.p.: 115° C. |
| 10 | $CF_3$ | $N(CH_3)_2$ | |
| 11 | $CF_3$ | $CH_2$–▷ | |
| 12 | $CF_3$ | ▷ | m.p.: 108° C. |
| 13 | $CF_3$ | $NH_2$ | m.p.: 163° C. |
| 14 | $CF_3$ | $CH_2$–▷(Cl)(Cl) | m.p.: 91° C. |
| 15 | $CF_3$ | 3-methylphenyl | |
| 16 | $CF_2CHF_2$ | $CH_3$ | m.p.: 79° C. |
| 17 | $CF_3$ | $CH_2$–$CH=CH_2$ | $^1$H NMR (CDCl$_3$, d): 4.40–4.42; 4.75–4.78 ppm |

TABLE 1-continued

Examples of the compounds of the formula (I) which can be prepared according to the invention

| Example No. | R¹ | R² | physical data |
|---|---|---|---|
| 18 | $CF_2CF_3$ | $n\text{-}C_4H_9$ | $^1H$ NMR ($CDCl_3$, d): 3.75–3.80; 11.75 ppm |
| 19 | $CHFCF_3$ | $CH_3$ | |
| 20 | $CH_2CF_3$ | $CH_3$ | |
| 21 | $CF_2C_2H_5$ | $CH_3$ | |
| 22 | $CHFCH_3$ | $CH_3$ | |
| 23 | $CF_2CH_3$ | $CH_3$ | |
| 24 | $CF_2CH_3$ | $C_2H_5$ | |

Starting substances of the formula (II):
Example (II-1):

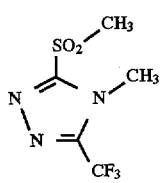

335 g (1.7 mol) of 4-methyl-3-trifluoromethyl-5-methylthio-4H-1,2,4-triazole are introduced into 2.5 liters of methylene chloride. To this there are added 5 g (4 mmol) of ammonium heptamolybdate tetrahydrate and 225 g (4.9 mol) of formic acid, the mixture is then refluxed, and 560 g of a 35% strength hydrogen peroxide solution (5.76 mol of $H_2O_2$) are added dropwise with vigorous stirring. Refluxing is continued for 16 hours; excess hydrogen peroxide is then removed using sodium hydrogen sulphite (39% strength aqueous solution), and the product is extracted three times using methylene chloride. The combined organic phases are washed using 5% strength aqueous sodium hydrogen sulphite solution and then with water, dried over magnesium sulphate and filtered.

The solvent is carefully removed from the filtrate by distillation under a water pump vacuum.

325 g (83.5% of theory) of 4-methyl-3-methylsulphonyl-5-trifluoromethyl-4H-1,2,4-triazole of melting point 96° C. are obtained.

Example (II-2)

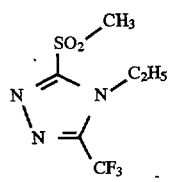

727.6 g (3.45 mol) of 4-ethyl-3-trifluoromethyl-5-methylthio-4H-1,2,4-triazole, 624 g of formic acid and 10 g of ammonium molybdate are introduced into 2 liters of dichloromethane. 2346 g of 30% strength hydrogen peroxide solution are added dropwise in the course of one hour at not more than 35° C. Stirring is continued for 8 hours (the reaction first still being exothermal). 2 liters of ice-water are added, excess hydrogen peroxide is removed by adding sodium hydrogen sulphite solution, the mixture is extracted repeatedly using dichloromethane, the combined organic phases are dried under sodium sulphate, and the solvent is evaporated on a rotary evaporator.

811.6 g (96.8% of theory) of 4-ethyl-3-trifluoromethyl-5-methylsulphonyl-4H-1,2,4-triazole are obtained as an oil.
$^1H$ NMR ($CDCl_3$, d) : 1.56–1.61; 3.60; 4.48–4.56 ppm.

Other examples of compounds of the formula (II) which can be prepared analogously are those listed in Table 2 below.

TABLE 2

Examples of the compounds of the formula (II)

| Example No. | R¹ | R² | R³ | Physical data |
|---|---|---|---|---|
| II-3 | $CF_3$ | $CH(CH_3)_2$ | $CH_3$ | $^1H$ NMR ($CDCl_3$, d): 1.69; 3.64; 5.12 ppm |
| II-4 | $CHF_2$ | $C_2H_5$ | $CH_3$ | m.p.: 51° C. |
| II-5 | $CF_2Cl$ | $CH_3$ | $CH_3$ | m.p.: 60° C. |
| II-6 | $CHF_2$ | $CH_3$ | $CH_3$ | m.p.: 98° C. |
| II-7 | $CF_2CHFCl$ | $CH_3$ | $CH_3$ | $^1H$ NMR ($CDCl_3$, d): 3.45; 4.15 ppm |
| II-8 | $CF_2CF_3$ | $CH_3$ | $CH_3$ | m.p.: 90° C. |
| II-9 | $CHF_2$ | cyclopropyl | $CH_3$ | m.p.: 106° C. |
| II-10 | $CF_3$ | phenyl | $CH_3$ | m.p.: 125° C. |
| II-11 | $CF_3$ | $N(CH_3)_2$ | $CH_3$ | |
| II-12 | $CF_3$ | $CH_2$-cyclopropyl | | |
| II-13 | $CF_3$ | cyclopropyl | $CH_3$ | $^1H$ NMR ($CDCl_3$, d): 3.42–3.50; 3.60 ppm |
| II-14 | $CF_3$ | $NH_2$ | $CH_3$ | m.p.: 101° C. |
| II-15 | $CF_3$ | $CH_2$-(2,2-dichlorocyclopropyl) | $CH_3$ | $^1H$ NMR ($CDCl_3$, d): 2.15–2.25; 3.62 ppm |
| II-16 | $CF_3$ | 3-methylphenyl | $CH_3$ | |
| II-17 | $CF_2CHF_2$ | $CH_3$ | $CH_3$ | m.p.: 79° C. |
| II-18 | $CF_3$ | $CH_2\text{--}CH=CH_2$ | $CH_3$ | m.p.: 68° C. |
| II-19 | $CF_2CF_3$ | $n\text{-}C_4H_9$ | $CH_3$ | m.p.: 72° C. |
| II-20 | $CHFCF_3$ | $CH_3$ | $CH_3$ | |
| II-21 | $CH_2CF_3$ | $CH_3$ | $CH_3$ | |
| II-22 | $CF_2C_2H_5$ | $CH_3$ | $CH_3$ | |
| II-23 | $CHFCH_3$ | $CH_3$ | $CH_3$ | |
| II-24 | $CF_2CH_3$ | $CH_3$ | $CH_3$ | |
| II-25 | $CF_2CH_3$ | $C_2H_5$ | $CH_3$ | |

Precursors of the formula (III):
Example (III-1)

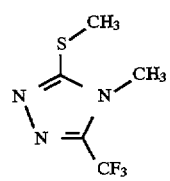

250 g (1.36 mol) of 4-methyl-5-trifluoromethyl-2,4-dihydro-3H-1,2,4-triazole-3-thione are introduced into 1.64 liters of ethanol. To this there are added 61.2 g (1.53 mol) of sodium hydroxide, whereupon a clear solution forms within one hour, the reaction having first being exothermic. 217 g (1.53 mol) of methyl iodide are subsequently added dropwise, and the mixture is stirred for 16 hours at 20° C. It is then concentrated to approximately half its volume, stirred with approximately 3 liters of ice-water, acidified using concentrated hydrochloric acid and extracted three times using methylene chloride. The combined organic phases are dried over magnesium sulphate and filtered. The solvent is carefully removed from the filtrate by distillation under a water pump vacuum.

207.4 g (77.4% of theory) of 4-methyl-3-methylthio-5-trifluoromethyl-4H-1,2,4-triazole are obtained as a yellow powder of melting point 46° C.

Example (III-2)

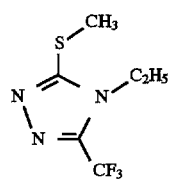

371.3 g (1.88 mol) of 4-ethyl-5-trifluoromethyl-2,4-dihydro-3H-1,2,4-triazoline-3-thione and 83.5 g (2.09 mol) of sodium hydroxide are introduced into 1.5 liters of ethanol. 296.8 g (2.09 mol) of iodomethane are added dropwise at not more than 30° C. (cooling), and stirring is continued for 8 hours at 20° C. The reaction solution is stirred with 1.5 liters of ice-water and extracted three times using dichloromethane; the combined organic phases are dried over sodium sulphate and evaporated.

371.4 g (93.6% of theory) of 4-ethyl-3-trifluoromethyl-5-methylthio-4H-1,2,4-triazole are obtained as an oil.

$^1$H NMR (CDCl$_3$, d): 1.40–1.45; 280; 4.04–4.10 ppm.

Other examples of the compounds of the formula (III) which can be prepared analogously are those listed in Table 3 below.

TABLE 3

Examples of the precursors of the formula (III)

| Example No. | R$^1$ | R$^2$ | R$^3$ | Physical data |
|---|---|---|---|---|
| III-3 | CF$_3$ | CH(CH$_3$)$_2$ | CH$_3$ | $^1$H NMR (CDCl$_3$, d): 1.58; 2.81; 4.63 ppm |
| III-4 | CHF$_2$ | C$_2$H$_5$ | CH$_3$ | $^1$H NMR (CDCl$_3$, d): 2.80; 4.08–4.15 ppm |
| III-5 | CF$_2$Cl | CH$_3$ | CH$_3$ | n$_D^{20}$ = 1.5154 |
| III-6 | CHF$_2$ | CH$_3$ | CH$_3$ | $^1$H NMR (CDCl$_3$, d): 2.78; 3.68 ppm |
| III-7 | CF$_2$CHFCl | CH$_3$ | CH$_3$ | m.p.: 43° C. |
| III-8 | CF$_2$CF$_3$ | CH$_3$ | CH$_3$ | $^1$H NMR (CDCl$_3$, d): 2.80; 3.68 ppm |
| III-9 | CHF$_2$ | ◁ | CH$_3$ | $^1$H NMR (CDCl$_3$, d): 2.78; 3.08–3.15 ppm |
| III-10 | CF$_3$ | phenyl | CH$_3$ | m.p.: 89° C. |
| III-11 | CF$_3$ | N(CH$_3$)$_2$ | CH$_3$ | |

TABLE 3-continued

Examples of the precursors of the formula (III)

| Example No. | R$^1$ | R$^2$ | R$^3$ | Physical data |
|---|---|---|---|---|
| III-12 | CF$_3$ | CH$_2$–◁ | CH$_3$ | |
| III-13 | CF$_3$ | ◁ | CH$_3$ | m.p.: 83° C. |
| III-14 | CF$_3$ | NH$_2$ | CH$_3$ | m.p.: 39° C. |
| III-15 | CF$_3$ | CH$_2$–cyclopropyl(Cl,Cl) | CH$_3$ | $^1$H NMR (CDCl$_3$, d): 2.00–2.10; 2.85 ppm |
| III-16 | CF$_3$ | o-tolyl | CH$_3$ | |
| III-17 | CF$_2$CHF$_2$ | CH$_3$ | CH$_3$ | $^1$H NMR (CDCl$_3$, d): 2.80; 3.70 ppm |
| III-18 | CF$_3$ | CH$_2$—CH=CH$_2$ | CH$_3$ | m.p.: 32° C. |
| III-19 | CF$_3$ | n-C$_4$H$_9$ | CH$_3$ | $^1$H NMR (CDCl$_3$, d): 1.35–1.48; 2.82 ppm |
| III-20 | CHFCF$_3$ | CH$_3$ | CH$_3$ | |
| III-21 | CH$_2$CF$_3$ | CH$_3$ | CH$_3$ | |
| III-22 | CF$_2$C$_2$H$_5$ | CH$_3$ | CH$_3$ | |
| III-23 | CHFCH$_3$ | CH$_3$ | CH$_3$ | |
| III-24 | CF$_2$CH$_3$ | CH$_3$ | CH$_3$ | |
| III-25 | CF$_2$CH$_3$ | C$_2$H$_5$ | CH$_3$ | |

Precursors of the formula (IV):
Example (IV-I)

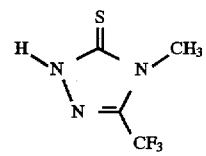

257 g (2.44 mol) of 4-methyl-thiosemicarbazide are added to 1.2 liters of trifluoroacetic acid and the mixture is refluxed for 16 hours. It is then concentrated under a water pump vacuum, the residue is triturated with diethyl ether/petroleum ether (5:100 by volume), and the product which has been obtained in crystalline form is isolated by filtration with suction.

444.5 g (95.5% of theory) of 4-methyl-5-trifluoromethyl-2,4-dihydro-3H-1,2,4-triazole-3-thione of melting point 115° C. are obtained.

Example (IV-2)

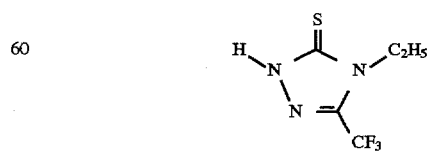

248 g (2.18 mol) of trifluoroacetic acid are added dropwise to 235.4 g (1.98 mol) of 4-ethyl-thiosemicarbazide in 1000 ml of xylene, during which process the temperature rises to 50° C. After 1 hour at reflux temperature, the water of reaction, which has formed, is removed on a water separator under reflux conditions in the course of 3 hours. When the reaction has ended, the reaction mixture is concentrated.

371.3 g of 4-ethyl-5-trifluoromethyl-2,4-dihydro-3H-1,2, 4-triazole-3-thione of melting point 93° C are obtained.

Other examples of compounds of the formula (IV) which can be prepared analogously are those listed in Table 4 below.

TABLE 4

Examples of the compounds of the formula (IV)

| Example No. | $R^1$ | $R^2$ | physical data |
|---|---|---|---|
| IV-3 | $CF_3$ | $CH(CH_3)_2$ | m.p.: 67° C. |
| IV-4 | $CHF_2$ | $C_2H_5$ | m.p.: 118° C. |
| IV-5 | $CF_2Cl$ | $CH_3$ | m.p.: 64° C. |
| IV-6 | $CHF_2$ | $CH_3$ | m.p.: 165° C. |
| IV-7 | $CF_2CHFCl$ | $CH_3$ | m.p.: 128° C. |
| IV-8 | $CF_2CF_3$ | $CH_3$ | m.p.: 77° C. |
| IV-9 | $CHF_2$ | cyclopropyl | m.p.: 139° C. |
| IV-10 | $CF_3$ | phenyl | m.p.: 144° C. |
| IV-11 | $CF_3$ | $N(CH_3)_2$ | m.p.: 152° C. |
| IV-12 | $CF_3$ | $CH_2$-cyclopropyl | m.p.: 77° C. |
| IV-13 | $CF_3$ | cyclopropyl | m.p.: 159° C. |
| IV-14 | $CF_3$ | $NH_2$ | m.p.: 109° C. |
| IV-15 | $CF_3$ | $CH_2$-(2,2-dichlorocyclopropyl) | m.p.: 87° C. |
| IV-16 | $CF_3$ | 3-methylphenyl | m.p.: 190° C. |
| IV-17 | $CF_2CHF_2$ | $CH_3$ | |
| IV-18 | $CF_3$ | $CH_2-CH=CH_2$ | m.p.: 65° C. |
| IV-19 | $CF_3$ | $n-C_4H_9$ | b.p.: 142°–145° C. |
| IV-20 | $CHFCF_3$ | $CH_3$ | |
| IV-21 | $CH_2CF_3$ | $CH_3$ | |
| IV-22 | $CF_2C_2H_5$ | $CH_3$ | |
| IV-23 | $CHFCH_3$ | $CH_3$ | |
| IV-24 | $CF_2CH_3$ | $CH_3$ | |
| IV-25 | $CF_2CH_3$ | $C_2H_5$ | |

Precursors of the formula (VI):
Example (VI-1):

$$H_2N-NH-\underset{\underset{S}{\|}}{C}-NH-CH_3$$

30 g (0.6 mol) of hydrazine hydrate are refluxed in 250 ml of ethanol, and a solution of 36.5 g (0.5 mol) of methyl isothiocyanate in 50 ml of ethanol is added dropwise in the course of 30 minutes. Stirring of the mixture under reflux conditions is continued for 10 minutes, and the mixture is then cooled to +5° C. and filtered off with suction.

45 g (86% of theory) of 4-methyl-thiosemicarbazide of melting point 138° C. are obtained.

Example (VI-2)

$$C_2H_5-NH-\underset{\underset{S}{\|}}{C}-NH-NH_2$$

1810 g (3.62 mol) of 10% strength hydrazine hydrate solution in water are introduced and cooled to 0°–5° C., with stirring. 300 g (3.45 mol) of ethyl isothiocyanate are added dropwise at 0°–5° C. in the course of 1 hour, stirring is continued for 2 hours, and the product which has precipitated is filtered off with suction. After the filtrate has been evaporated, both residues are combined. 79 g of 4-ethyl-thiosemicarbazide of melting point 85° C. are obtained.

It will be understood that the specification and examples are illustrative but not limitative of the present invention and that other embodiments within the spirit and scope of the invention will suggest themselves to those skilled in the art.

What is claimed is:

1. An alkylsulphonyltriazole derivative of the formula

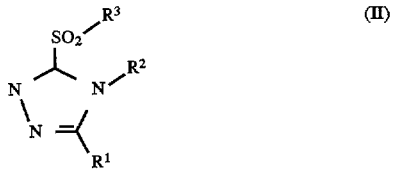

wherein $R^1$ represents alkyl having 1 to 6 carbon atoms which is optionally substituted by halogen, cyano or $C_1-C_4$-alkoxy, or represents a cycloalkyl having 3 to 6 carbon atoms which is optionally substituted by halogen, cyano or $C_1-C_4$-alkyl and $R^2$ represents amino, or represents alkyl, alkenyl, alkinyl, alkoxy, alkylamino or dialkylamino, each of which has up to 6 carbon atoms in the alkyl, alkenyl or alkinyl groups and each of which is optionally substituted by halogen, cyano or $C_1-C_4$-alkoxy, or represents $C_3-C_6$-cycloalkyl, $C_3-C_6$-cycloalkyl-$C_1-C_2$-alkyl or phenyl, each of which is optionally substituted by halogen, cyano, $C_1-C_4$-alkyl, $C_1-C_4$-alkoxy or $C_1-C_4$-alkoxycarbonyl, and $R^3$ is alkyl having 1 to 4 carbon atoms.

2. An alkylsulphonyltriazole derivative according to claim 1, in which $R^1$ represents methyl, ethyl, n- or i-propyl or n-, i- or s-butyl, each of which is optionally substituted by fluorine, chlorine, bromine, cyano, methoxy or ethoxy, or represents cyclopropyl, cyclopropylmethyl, cyclobutyl, cyclopentyl or cyclohexyl, each of which is optionally substituted by fluorine, chlorine, bromine, cyano or methyl, and $R^2$ represents amino, or represents methyl, ethyl, n- or i-propyl, n-, i - or s -butyl, allyl, propargyl, methoxy, ethoxy, n- or i-propoxy, n- , i- or s-butoxy, methylamino, ethylamino, n- or i-propylamino, n-, i - or s -butylamino, dimethylamino or diethylamino, each of which is optionally substituted by fluorine, chlorine, cyano, methoxy or ethoxy, or represents cyclopropyl, cyclobutyl, cyclopentyl, cyclohexyl or phenyl, each of which is optionally substituted by fluorine, chlorine, bromine, cyano, methyl, ethyl, n- or i-propyl, methoxycarbonyl or ethoxy-carbonyl, and $R^3$ is alkyl having 1 to 4 carbon atoms.

3. An alkylsulphonyltriazole derivative according to claim 1, wherein $R^1$ is alkyl having 1 to 6 carbon atoms which is substituted by halogen, $R^2$ is amino, or is alkyl, alkenyl, alkinyl, alkoxy, alkylamino or dialkylamino, each of which has up to 6 carbon atoms in the alkyl, alkenyl or alkinyl groups and each of which is optionally substituted by halogen, cyano or $C_1$–$C_4$-alkoxy, or is $C_3$–$C_6$-cycloalkyl, $C_3$–$C_6$-cycloalkyl-$C_1$–$C_2$-alkyl or phenyl, each of which is optionally substituted by halogen, cyano, $C_1$–$C_4$-alkyl, $C_1$–$C_4$-alkoxy or $C_1$–$C_4$-alkoxy-carbonyl, and $R^3$ is alkyl having 1 to 4 carbon atoms.

4. An alkylsulphonyltriazole derivative according to claim 3, wherein $R^1$ is alkyl having 1 to 6 carbon atoms which is substituted by fluorine.

5. An alkylsulphonyltriazole derivative according to claim 1, wherein $R^1$ is methyl, ethyl, n- or i-propyl or n-, i- or s-butyl, each of which is substituted by at least one of fluorine, chlorine, and bromine, and $R^2$ is amino, or is methyl ethyl, n- or i-propyl or n-, i- or s-butyl, allyl, propargyl, methoxy, ethoxy, n-or i-propoxy, n-, i-or s-butoxy, methylamino, ethylamino, n- or i-propylamino, n-, i- or s-butylamino, dimethylamino or diethylamino, each of which is optionally substituted by fluorine, chlorine, cyano, methoxy or ethoxy, or is cyclopropyl, cyclobutyl, cyclopentyl, cyclohexyl or phenyl, each of which is optionally substituted by fluorine, chlorine, bromine, cyano, methyl, ethyl, n- or i-propyl, methoxy-carbonyl or ethoxy-carbonyl, and $R^3$ is methyl or ethyl.

6. An alkylsulphonyl triazole derivative according to claim 1, wherein $R^1$ is methyl ethyl, n- or i-propyl, cyclopropyl or cyclopropylmethyl, each of which is mono-, di-, tri-, tetra-, penta-, hexa- or heptasubstituted with at least one of fluorine and chlorine, and $R^2$ is methyl, ethyl, n- or i-propyl, methoxy, ethoxy, methylamino, ethylamino, dimethylamino, cyclopropyl, phenyl or tolyl, and $R^3$ is alkyl having 1 to 4 carbon atoms.

* * * * *

UNITED STATES PATENT AND TRADEMARK OFFICE
CERTIFICATE OF CORRECTION

PATENT NO. : 5,739,349
DATED : April 14, 1998
INVENTOR(S) : Linker, et al.

It is certified that error appears in the above-indentified patent and that said Letters Patent is hereby corrected as shown below:

| | |
|---|---|
| Title Page | OTHER PUBLICATIONS: Insert -- Chemical Abstracts, vol. 88 No. 17, Abstract Number 88,130169a (1978) -- |
| Col. 12, line 57 | Delete " cyciobutyl " and substitute -- cyclobutyl -- |

Signed and Sealed this

Twelfth Day of September, 2000

Attest:

Q. TODD DICKINSON

Attesting Officer

Director of Patents and Trademarks